(12) United States Patent
Cheng et al.

(10) Patent No.: US 10,233,430 B1
(45) Date of Patent: Mar. 19, 2019

(54) GLUCOSE OXIDASE HAVING IMPROVED THERMOSTABILITY

(71) Applicant: Dongguan APAC Biotechnology CO., Ltd., DongGuan (CN)

(72) Inventors: Ya-Shan Cheng, New Taipei (TW); Tzu-Hui Wu, New Taipei (TW); Cheng-Yen Lin, New Taipei (TW); Hui-Lin Lai, New Taipai (TW); Cheng-Bin Zheng, New Taipei (TW); Ting-Yung Huang, New Taipei (TW); I-Hsuan Lin, New Taipei (TW); Jian-Wen Huang, New Taipei (TW); Chun-Chi Chen, New Taipei (TW); Rey-Ting Guo, New Taipei (TW)

(73) Assignee: DONGGUAN APAC BIOTECHNOLOGY CO.,LTD., Dongguan (CN)

( * ) Notice: Subject to any disclaimer, the term of this patent is extended or adjusted under 35 U.S.C. 154(b) by 0 days.

(21) Appl. No.: 16/130,859

(22) Filed: Sep. 13, 2018

(30) Foreign Application Priority Data

Oct. 13, 2017 (TW) .............................. 106135046 A

(51) Int. Cl.
*C12N 9/04* (2006.01)
*C12N 15/52* (2006.01)

(52) U.S. Cl.
CPC ........... *C12N 9/0006* (2013.01); *C12N 15/52* (2013.01); *C12Y 101/03004* (2013.01)

(58) Field of Classification Search
CPC .................................................... C12N 9/0006
See application file for complete search history.

(56) References Cited

FOREIGN PATENT DOCUMENTS

CN         107189991 A       9/2017

OTHER PUBLICATIONS

Halalipour et al., Glucose Oxidase Stabilization Against Thermal Inactivation Using High Hydrostatic Pressure and Aydrophobic Modification, Biotechnol Bioeng. Mar. 2017; 114(3): 516-525.
NCBI PDB: 1CF3_A, Chain A, Glucose Oxidase from Aperguillus Niger, Jul. 31, 2018.

*Primary Examiner* — Maryam Monshipouri
(74) *Attorney, Agent, or Firm* — Kirton McConkie; Evan R. Witt

(57) ABSTRACT

A glucose oxidase having improved thermostability is disclosed. The amino acid sequence of the glucose oxidase is a modified amino acid sequence of SEQ ID NO: 2, wherein the modification is a substitution of glutamate at position 129 with proline, and/or a substitution of glutamine at position 243 with valine.

9 Claims, 6 Drawing Sheets
Specification includes a Sequence Listing.

FIG. 1

| Mutant | Mutagenic Primer Sequence |
|---|---|
| E129P | 5'-GGGAAACTGTCTTCGGAAACCCAGGTTGGAATTGGGATAATGTTG-3'<br>(SEQ ID NO: 3) |
| Q243V | 5'-CTAATTACCAAAGACCAAACTTGGTTTGTTTTGACTGGTCAGTATG-3'<br>(SEQ ID NO: 4) |

FIG. 2

```
tctaacggaatcgaggcttctttgttgacagaccctaaagacgttctggaagaactgtcgattacatcattgccggtggtggtttgacc
 S  N  G  I  E  A  S  L  L  T  Q  F  K  D  V  S  G  K  T  V  D  Y  I  I  A  G  G  G  L  T ggattgacaactgccgctagattgaccgaaaatccaatatctctgttttggtcatcgagtctggatcttacgaatctgacagaggacca
 G  L  T  T  A  A  R  L  T  E  N  P  N  I  S  V  L  V  I  E  S  G  S  Y  E  S  D  R  G  P attatcgaggatttgaacgcataaggtgacatcttcggtcttctgttgatcatgcatacgaaacagttgaattggctactaacaatcaa
 I  I  E  D  L  N  A  Y  G  D  I  F  G  S  S  V  D  R  A  Y  E  T  V  E  L  A  T  N  N  Q acagctttgattagatctggtaacggattgggtggttctacattggtcaacggaggtacttggactagaccacataaggccaggtcgat
 T  A  L  I  R  S  G  N  G  L  G  G  S  T  L  V  N  G  G  T  W  T  R  P  H  K  A  Q  V  D tcttgggaaactgtcttcggaaacccaagtgtggaattgggataagttgctgcatatctttgcaggcgaaagagctagagcccaaac
 S  W  E  T  V  F  G  N  P  S  N  N  D  N  V  A  A  Y  S  L  Q  A  E  R  A  R  A  P  N gctaagcaaattgctgctggtcattactttaatgcttcttgtcatggagttaacggtactgttcatgccggaccaagagatacaggtgac
 A  K  Q  I  A  A  G  H  Y  F  N  A  S  C  H  G  V  N  G  T  V  H  A  G  P  R  D  T  G  D gattactctccaattgttaaagccttgatgtctgctgttgaggatagaggtgtccctactaagaaagactttggatgtggtgacccacac
 D  Y  S  P  I  V  K  A  L  M  S  A  V  E  D  R  G  V  P  T  K  K  D  F  G  C  G  D  P  H ggtgtctctatgttccctaaccattgcatgaggatcaggtcagatctgatgctgctagaatggttgttgctaattaccaaagacca
 G  V  S  M  F  P  N  H  C  M  E  D  Q  V  R  S  D  A  A  R  E  W  L  L  P  N  Y  Q  R  P aacttgcaggttttgactggtcagtatgttggaaaggtcttgttgtctcaaaacggaactaccccaagagccgttggagtcgaattggt
 N  L  Q  V  L  T  G  Q  Y  V  G  K  V  L  L  S  Q  N  G  T  T  P  R  A  V  G  V  E  L  V actcataagggtaacactcacaacgtttatgctaaacatgaagttttgttggcagctggttctgcagtttctccaactatcttggaatac
 T  H  K  G  N  T  H  N  V  Y  A  K  H  E  V  L  L  A  A  G  S  A  V  S  P  T  I  L  E  Y tctggtattggtatgaaatctatttgggaccattgggtattgatactgtcgttgattgccagtggattgaattgcaagaccagaca
 S  G  I  G  M  K  S  I  L  E  P  L  G  I  D  T  V  V  D  L  P  V  G  L  N  L  Q  D  Q  T accgctacagttagatctagaattacttctgccggagcaggacaaggacaggctgcctggttcgctacttttaacgagacttttggtgac
 T  A  T  V  R  S  R  I  T  S  A  G  A  G  Q  G  Q  A  A  W  F  A  T  F  N  E  T  F  G  D tatctgagaaggcaatgagttgttgaataccaagttggaacagtgggctgaagaggctgtcgcaagaggtggattccacaacactaca
 Y  S  E  K  A  H  E  L  E  N  Y  K  L  E  Q  W  A  E  E  A  V  A  R  G  G  F  H  N  T  T gcattgttgattcaatatgagaactacagagactggattgtcaaccataacgttgcttactctgaattgtctttggatacagccggtgtt
 A  L  L  I  Q  Y  E  N  Y  R  D  W  I  V  N  H  N  V  A  Y  S  E  L  F  I  D  T  A  G  V gcatctttcgacgtctgggatttgttgccattcacaagaggatacgttcacatcttggataaggatccatacttgcaccatttcgcctat
 A  S  F  D  V  W  D  L  L  P  F  T  R  G  Y  V  H  I  L  D  K  D  P  Y  L  H  H  F  A  Y gatccacaatactccttgaacgaattggacttgttgggtcaagccgctgcaactcagttggctagaaacatttctaattctggagctatg
 D  P  Q  Y  F  L  N  E  L  D  L  L  G  Q  A  A  A  T  Q  L  A  R  N  I  S  N  S  G  A  M caaactcatttcgcaggtgaaactattcctggtgacaatttggcatatcaagcagatttgtctgcatggactgaatacattccatcccat
 Q  T  Y  F  A  G  E  T  I  P  G  D  N  L  A  Y  Q  A  D  L  S  A  W  T  E  Y  I  P  Y  H tttagacctaactatcatggtgtcggaacttgttctatgatgcctaaggaaatggttggagttgtcgataacgccgcagagtctacggt
 F  R  P  N  Y  H  G  V  G  T  C  S  M  M  P  K  E  M  G  G  V  V  D  N  A  A  R  V  Y  G gttcaaggtttgagagttattgatggatctattccaccaacacaaatgtcttctcatgttatgacagtcttctacgctatggcattgaaa
 V  Q  G  L  R  V  I  D  G  S  I  P  P  T  Q  M  S  S  H  V  M  T  V  F  Y  A  M  A  L  K atctctgacgcaattttggaagattacgcttctatgcag      -SEQ ID NO: 5
 I  S  D  A  I  L  E  D  Y  A  S  M  Q       -SEQ ID NO: 6
```

FIG. 3

```
tctaacggaatcgaggcttctttgttgacagaccctaaagacgttttctggaagaactgtcgattacatcattgccggtggtggtttgacc
 S  N  G  I  E  A  S  L  L  T  D  P  K  D  V  S  G  R  T  V  D  Y  I  I  A  G  G  L  T ggattgacaactgccgctagattgaccgaaaatccaaatatctctgttttggtcatcgagtctggatcttacgaatctgacagaggacca
 G  L  T  T  A  A  R  L  T  E  N  P  N  I  S  V  L  V  I  E  S  G  S  Y  E  S  D  R  P attatcgaggatttgaacgcatacggtgacatcttcggttcttctgttgatcatgcatacgaaacagttgaattggctactaacaatcaa
 I  I  E  D  L  N  A  Y  G  D  I  F  G  S  S  V  D  H  A  Y  E  T  V  E  L  A  T  N  N  Q acagctttgattagatctggtaacggattgggtggttctacattggtcaacggaggtacttggactagaccacataaggcccaggtcgat
 T  A  L  I  R  S  G  N  G  L  G  G  S  T  L  V  N  G  G  T  W  T  R  P  H  K  A  Q  V  D tcttgggaaactgtcttcggaaacgaagttggaattggataatgttgctgcatatctttgcaggcagaaagagctagagccccaaac
 S  W  E  T  V  F  G  N  E  G  N  N  W  D  N  V  A  A  Y  S  L  Q  A  E  R  A  R  A  P  N gctaagcaaattgctgctggtcattactttaatgcttcttgtcatggagttaacggtactgttcatgccggaccaagagatacaggtgac
 A  K  Q  I  A  A  G  H  Y  F  N  A  S  C  H  G  V  N  G  T  V  H  A  G  P  R  D  T  G  D gattactctccaattgttaaagccttgatgtctgctgttgaggatagaggtgtccctactaagaagacctttggatgtggtgacccacac
 D  Y  S  P  I  V  K  A  L  M  S  A  V  E  D  R  G  V  P  T  K  K  T  F  G  C  G  D  P  H ggtgtctctatgttcccctaacacattgcatgaggatcaggtcagatctgatgctgctagagaatggttgttgcctaattaccaaagacca
 G  V  S  M  F  P  N  T  L  H  E  D  Q  V  R  S  D  A  A  R  E  W  L  L  P  N  Y  Q  R  P aacttgtcgttcttgactggtcagtatgttggaaaggtcttgttgtctcaaaacggaactaccccaagagccgttggagtcgaatttggt
 N  L  V  V  L  T  G  Q  Y  V  G  K  V  L  L  S  Q  N  G  T  T  P  R  A  V  G  V  E  F  G actcataagggtaacactcacaacgttatgctaaacatgaagtttgttggcagctggttctgcagtttctccaactatcttggaatac
 T  H  K  G  N  T  H  N  V  M  L  N  M  K  F  V  G  S  W  F  C  S  F  S  N  Y  L  E  Y tctggtattggtatgaaatctatttggagccattgggtattgatactgtcgttgattgccagttggattgaatttgcaagaccagaca
 S  G  I  G  M  K  S  I  L  E  P  L  G  I  D  T  V  V  D  L  P  V  G  L  N  L  Q  D  Q  T accgctacagttagatctagaattacttctgccggagcaggacaaggacaggctgcctggttgctacttttaacgagactttggtgac
 T  A  T  V  R  S  R  I  T  S  A  G  A  G  Q  S  Q  A  A  W  F  A  T  F  N  E  T  F  G  D tattctgagaaggcacatgagttgttgaatactaagttggaacagtgggctgaagaggctgtccaagaggtggattccacaacactaca
 Y  S  E  E  A  H  E  L  L  N  T  K  L  E  Q  W  A  E  E  A  V  R  G  G  F  N  T  T gcattgttgattcaatatgagaactacagagactggattgtcaaccataacgttgcttactctgaattgttttggatacagccggtgtt
 A  L  L  I  Q  Y  E  N  Y  R  D  W  I  V  N  H  N  V  A  Y  S  E  L  F  L  D  T  A  G  V gcatcttccgacgtctgggatttgttgccattcacaagaggatacgttcacatcttggataaggatccatacttgcaccatttcgcctat
 A  S  F  D  V  W  D  L  L  P  F  T  R  G  Y  V  H  I  L  D  K  D  P  Y  L  H  H  F  A  Y gatccacaatacttcttgaacgaattggacttgttgggtcaagccgctgcaactcagttggctagaaacatttctaattctggagctatg
 D  P  Q  Y  F  L  N  E  L  D  L  L  G  Q  A  A  A  T  Q  L  A  R  N  I  S  N  S  G  A  M caaacttatttcgcaggtgaaactattcctggtgacaatttggcatatgacgcagatttgtctgcatggactgaatacattccataccat
 Q  T  Y  F  A  G  E  T  I  P  G  D  N  L  A  Y  D  A  G  L  S  A  W  T  E  Y  I  P  Y  H tttagacctaactatcatggtgtcggaacttgttctatgatgcctaaggaaatgggtggagttgtcgataacgccgcagagtctacggt
 F  R  P  N  Y  H  G  V  G  T  C  S  M  M  P  K  E  M  G  G  V  V  D  N  A  A  R  V  Y  G gttcaaggtttgagagttattgatggatctattccaccaacacaaatgtcttctcatgttatgacagtcttctacgctatggcattgaaa
 V  Q  G  L  R  V  I  D  G  S  I  P  P  T  Q  M  S  S  H  V  M  T  V  F  Y  A  M  A  L  K atctctgacgcaatttggaagattacgcttctatgcag     -SEQ ID NO: 7
 I  S  D  A  I  L  E  D  Y  A  S  M  Q       -SEQ ID NO: 8
```

GLUCOSE OXIDASE HAVING IMPROVED THERMOSTABILITY

FIELD OF THE INVENTION

The present invention relates to a glucose oxidase, and more particularly to a glucose oxidase having improved thermostability.

BACKGROUND OF THE INVENTION

Glucose oxidase (β-D-glucose: oxygen 1-oxidoreductase; EC1.1.3.4) specifically catalyzes oxidation of β-D-glucose to gluconic acid and simultaneously production of $H_2O_2$ by using $O_2$ as an electron acceptor. Glucose oxidase was firstly discovered in the extracts from *Aspergillus niger* by Muller's lab in 1928. Glucose oxidase is wildly produced by animals, plants and microorganisms, and most researches focus on microbial glucose oxidase. Microbial glucose oxidase mainly exists in *A. niger* and *Penicillium* spp. Industrial glucose oxidase is also obtained by these two natural producing strains. However, the production and enzymatic activity of glucose oxidase originally expressed from the natural sources are not good enough. Besides, *A. niger* and *Penicillium* spp. simultaneously produce glucose oxidase and other kinds of proteins that cause the difficulty in protein purification during industrial producing process, and finally lead to high cost of industrial production. Hence, there are more and more researches about the production of glucose oxidase by other microbial expression systems, especially by *Pichia pastoris* which is commonly used in industrial applications.

Glucose oxidase is widely used in many industrial applications for years. It can be used as an antioxidant to preserve food and maintain the flavor of beer in food industry. Besides, it is one of bread/dough-improving additives in baking industry. Glucose oxidase is also used as a glucose biosensor which measures blood glucose levels for diabetes monitoring, for example. Additionally, $H_2O_2$ produced by glucose oxidase is capable of bleaching in textile industry. In recent years, glucose oxidase is extensively used in feed industry. It can reduce oxygen levels, produce $H_2O_2$, and decrease environmental pH value because of produced gluconic acid, and thus can further inhibit the growth of some bacteria or fungi. Therefore, glucose oxidase is used as a feed additive to improve the gut environment in animals. Moreover, glucose oxidase is possible to be used in biofuel production. To sum up, glucose oxidase plays a critical role in many different industrial applications. Thus, there are increasing researches about enhancement of its catalytic efficiency and protein production and improvement of its protein properties such as thermostability and pH stability.

Currently, many researches try to obtain better enzymes by either screening in nature or modifying present enzymes. In the present invention, glucose oxidase is modified by rational design to increase its thermostability, so as to further increase its application potential and economic value in industry.

SUMMARY OF THE INVENTION

An object of the present invention is to modify a glucose oxidase by means of structural analysis and site-directed mutagenesis for improving the thermostability of the glucose oxidase and further increasing its application potential and economic value in industry.

According to an aspect of the present invention, there is provided a glucose oxidase comprising a modified amino acid sequence of SEQ ID NO: 2, wherein the modification is a substitution of glutamate at position 129 with proline, and a substitution of glutamine at position 243 with valine. The gene encoding the amino acid sequence of SEQ ID NO: 2 is AnGOD gene isolated from *Aspergillus niger*. The glucose oxidase has a full length amino acid sequence of SEQ ID NO: 10.

According to another aspect of the present invention, there is provided a glucose oxidase comprising a modified amino acid sequence of SEQ ID NO: 2, wherein the modification is a substitution of glutamate at position 129 with proline. The gene encoding the amino acid sequence of SEQ ID NO: 2 is AnGOD gene isolated from *Aspergillus niger*. The glucose oxidase has a full length amino acid sequence of SEQ ID NO: 6.

According to an additional aspect of the present invention, there is provided a glucose oxidase comprising a modified amino acid sequence of SEQ ID NO: 2, wherein the modification is a substitution of glutamine at position 243 with valine. The gene encoding the amino acid sequence of SEQ ID NO: 2 is AnGOD gene isolated from *Aspergillus niger*. The glucose oxidase has a full length amino acid sequence of SEQ ID NO: 8.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the nucleotide sequence and the amino acid sequence of the wild type glucose oxidase AnGOD;

FIG. 2 shows the mutagenic primer sequences for site-directed mutagenesis;

FIG. 3 shows the nucleotide sequence and the amino acid sequence of the E129P mutant;

FIG. 4 shows the nucleotide sequence and the amino acid sequence of the Q243V mutant;

FIG. 5 shows the nucleotide sequence and the amino acid sequence of the E129P/Q243V mutant.

DETAILED DESCRIPTION OF THE PREFERRED EMBODIMENT

Figure 6:
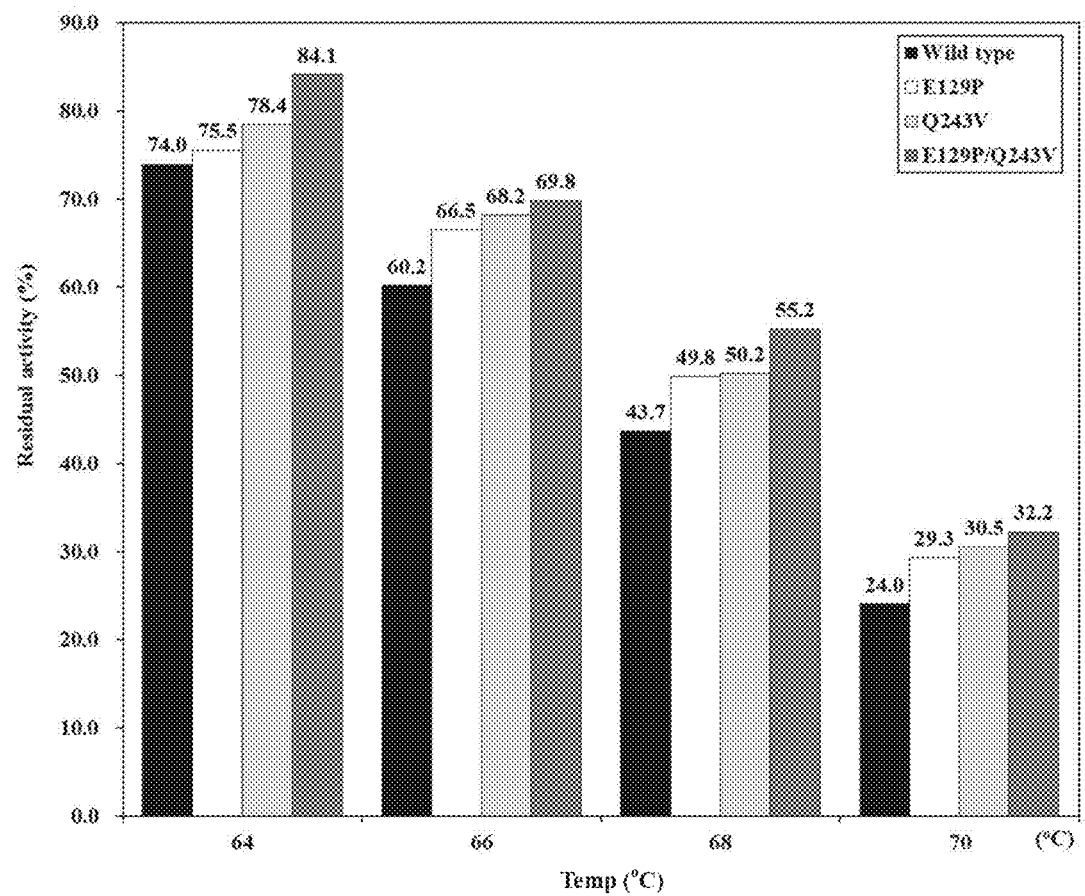
FIG. 6 shows the thermostability analysis of the wild type AnGOD and the three mutants.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The glucose oxidase employed in the present invention is encoded by AnGOD gene isolated from the filamentous fungus *Aspergillus niger*. According to previous studies, the optimal reaction temperature and pH of the glucose oxidase AnGOD are 37° C. and pH 6.0. In the present invention, the AnGOD gene was cloned into a vector and transformed into *Pichia pastoris* for protein expression. To improve the thermostability of the glucose oxidase AnGOD, the present invention analyzed its protein structure and chose some potential amino acids for modifications by site-directed mutagenesis.

The stability of protein structure has great correlation with its thermostability, and the hydrophobic interaction is one of the crucial effects on protein stability. Therefore, the present invention analyzed the protein structure of the glucose oxidase AnGOD, and tried to strengthen the stability of the protein structure by increasing the hydrophobic interaction within the protein structure, so as to further improve the thermostability of the enzyme. After analysis, Glu129 located on a loop and Gln243 located on a β-sheet were chosen for further modifications. By site-directed mutagenesis, Glu129 was singly mutated to proline as E129P mutant, while Gln243 was singly mutated to valine as Q243V mutant. These two mutation sites were even combined into E129P/Q243V double mutant. The above mutations all successfully improved the thermostability of the glucose oxidase AnGOD.

The enzyme modification processes and the resulted glucose oxidase are described in detail as follows.

Figure 1:
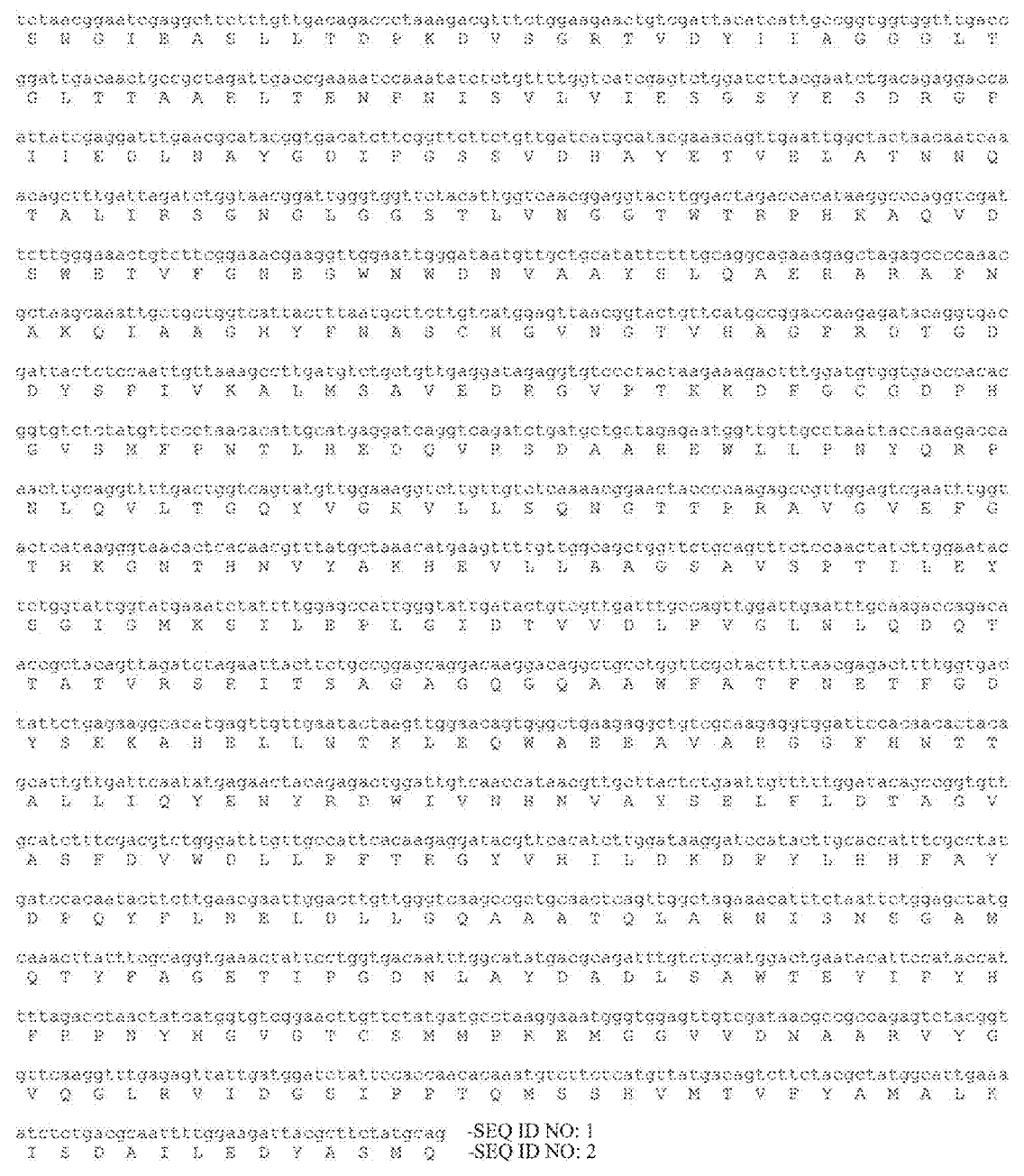

FIG. 1 shows the nucleotide sequence and the amino acid sequence of the wild type glucose oxidase AnGOD, wherein the AnGOD gene includes 1749 base pairs (the nucleotide sequence was numbered as SEQ ID NO: 1) and encodes 583 amino acids (the amino acid sequence was numbered as SEQ ID NO: 2). First, the AnGOD gene was cloned into pPICZaA vector. The plasmid DNA was linearized by restriction enzyme and then transformed into *Pichia pastoris*. The transformed cells were screened on YPD plates with 0.1 mg/ml zeocin at 30° C. for 2 days. The screened clones were selected and inoculated in YPD medium at 30° C. overnight. The proliferated cells were transferred into BMMY medium with 0.5% methanol for induction of protein expression. The supernatant containing the induced protein was collected by centrifugation for following analysis.

The three mutated genes of AnGOD were obtained by site-directed mutagenesis. Particularly, these mutated sequences were obtained by PCR method using the wild-type AnGOD gene as the template and using the mutagenic primers shown in FIG. 2. E129P means the glutamate at position 129 was substituted with proline, and the mutagenic primer E129P was numbered as SEQ ID NO: 3. Q243V means the glutamine at position 243 was substituted with valine, and the mutagenic primer Q243V was numbered as SEQ ID NO: 4. Therefore, the three mutated genes of AnGOD obtained by site-directed mutagenesis in the present invention were E129P, Q243V and E129P/Q243V.

Figure 5:
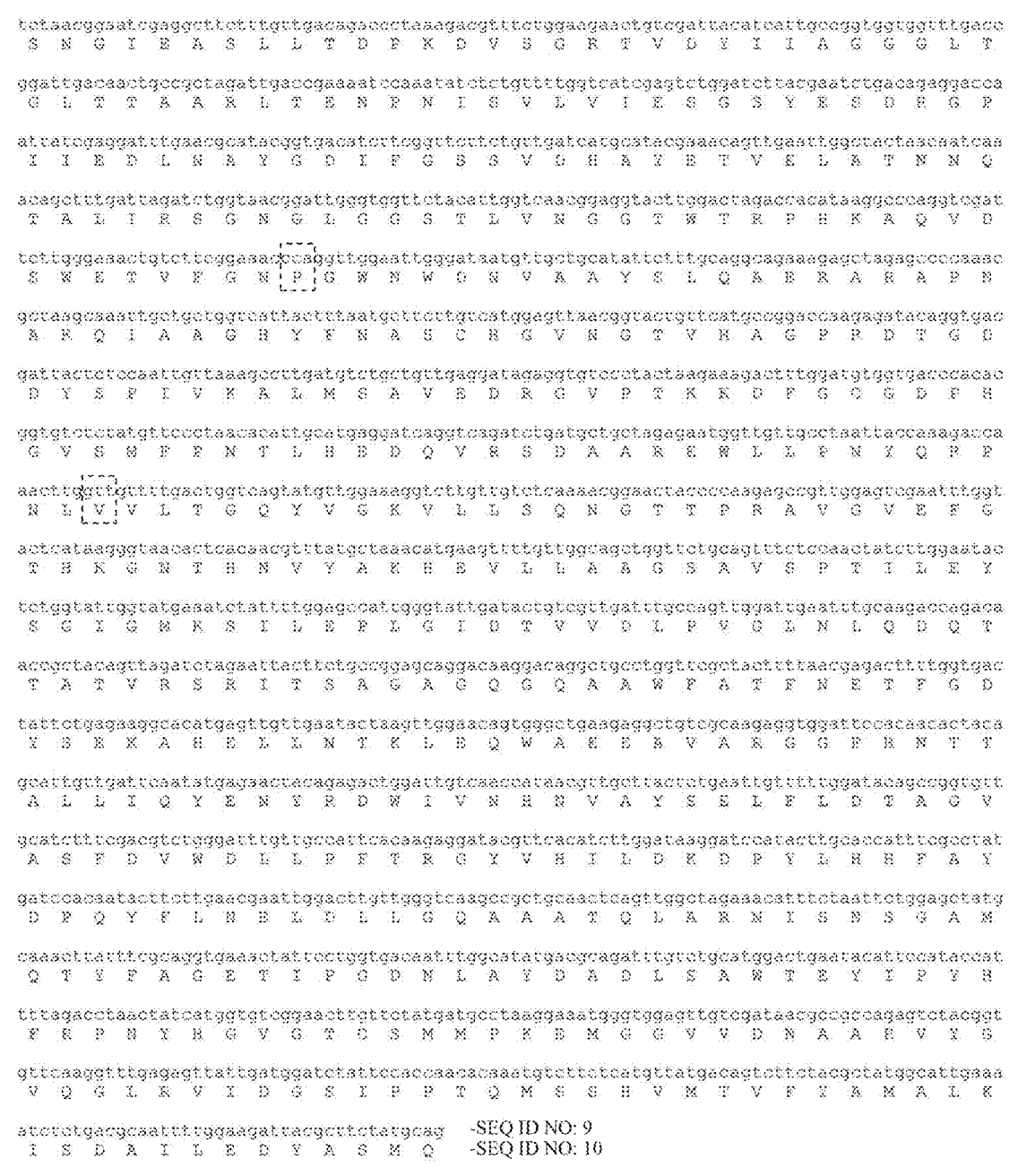

FIGS. 3 to 5 show the nucleotide sequences and the amino acid sequences of the three mutants. FIG. 3 shows the nucleotide sequence and the amino acid sequence of the E129P mutant, wherein the nucleotide sequence was numbered as SEQ ID NO: 5, the amino acid sequence was numbered as SEQ ID NO: 6, and the glutamate at position 129 was substituted with proline. FIG. 4 shows the nucleotide sequence and the amino acid sequence of the Q243V mutant, wherein the nucleotide sequence was numbered as SEQ ID NO: 7, the amino acid sequence was numbered as SEQ ID NO: 8, and the glutamine at position 243 was substituted with valine. FIG. 5 shows the nucleotide sequence and the amino acid sequence of the E129P/Q243V mutant, wherein the nucleotide sequence was numbered as SEQ ID NO: 9, the amino acid sequence was numbered as SEQ ID NO: 10, and the glutamate at position 129 was substituted with proline and the glutamine at position 243 was substituted with valine.

The original DNA template was removed by DpnI. The three mutated genes were individually transformed into *E. coli*. The success of gene mutation was confirmed by DNA sequencing. Finally, the three mutated genes were separately transformed into *P. pastoris* and then induced for expressing the mutated proteins by the same method mentioned above. Afterwards, the wild type protein and the mutated proteins were further analyzed for their enzymatic activity and thermostability.

The activity analysis of glucose oxidase is based on the principle that glucose oxidase catalyzes the oxidation of glucose and produces gluconic acid and $H_2O_2$. Then, $H_2O_2$ can oxidize o-dianisidine, which is a chromogenic agent, by catalyzation of horseradish peroxidase, and result in color change that can be measured and further calculated to determine the enzymatic activity of glucose oxidase. Basically, 2.5 ml of o-dianisidine, 0.3 ml of 18% glucose and 0.1 ml of horseradish peroxidase (90 unit/ml) were mixed and preheated in a water bath at 37° C. Subsequently, 0.1 ml of the diluted protein sample was added in the above mixture at 37° C. for 3 min. Then, 2 ml of sulfuric acid was added to stop the reaction. Finally, the absorption of OD540 nm was detected to determine the activity of glucose oxidase.

For the thermostability analysis of glucose oxidase, the normalized protein samples of the wild type and the mutated proteins were individually treated at 64° C., 66° C., 68° C. and 70° C. for 2 min and subsequently cooled on ice for 5 min and then recovered at room temperature for 5 min. Finally, the activity of the untreated sample and the residual activities of the heat-treated samples were determined by the activity analysis method mentioned above, wherein the activity of the untreated sample was set to 100% as control.

FIG. 6 shows the thermostability analysis of the wild type AnGOD and the three mutants. As shown in FIG. 6, the three mutants including E129P, Q243V and E129P/Q243V all showed higher thermostabilities compared to the wild type AnGOD under different conditions of heat treatments from 64° C. to 70° C. Take the result of heat treatment at 68° C. as an example; the residual activity of the wild type AnGOD was 43.7% while the residual activities of the mutants E129P and Q243V were 49.8% and 50.2%, respectively. Furthermore, the residual activity of the double mutant E129P/Q243V was 55.2%. It is clear that the single mutants E129P and Q243V both can enhance the thermostability of AnGOD, and the combination of these two mutation sites, i.e. the double mutant E129P/Q243V, can further increase at least 10% degree of the thermostability of AnGOD.

In conclusion, to improve the thermostability of the glucose oxidase AnGOD, the present invention chose some potential amino acids according to its structural analysis and further modified this enzyme by rational design. As a result, the three mutants including E129P, Q243V and E129P/Q243V all showed higher thermostabilities compared to the wild type AnGOD. Therefore, the present invention successfully improves the thermostability of the glucose oxidase AnGOD and further increases its economic value of industrial application and the possibility of expanding its industrial application range.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A glucose oxidase comprising a modified amino acid sequence of SEQ ID NO: 2, wherein the modification is a substitution of glutamate at position 129 with proline, and a substitution of glutamine at position 243 with valine.

2. The glucose oxidase according to claim 1 wherein a gene encoding the amino acid sequence of SEQ ID NO: 2 is AnGOD gene isolated from *Aspergillus niger*.

3. The glucose oxidase according to claim 1 having a full length amino acid sequence of SEQ ID NO: 10.

4. A glucose oxidase comprising a modified amino acid sequence of SEQ ID NO: 2, wherein the modification is a substitution of glutamate at position 129 with proline.

5. The glucose oxidase according to claim 4 wherein a gene encoding the amino acid sequence of SEQ ID NO: 2 is AnGOD gene isolated from *Aspergillus niger*.

6. The glucose oxidase according to claim 4 having a full length amino acid sequence of SEQ ID NO: 6.

7. A glucose oxidase comprising a modified amino acid sequence of SEQ ID NO: 2, wherein the modification is a substitution of glutamine at position 243 with valine.

8. The glucose oxidase according to claim 7 wherein a gene encoding the amino acid sequence of SEQ ID NO: 2 is AnGOD gene isolated from *Aspergillus niger*.

9. The glucose oxidase according to claim 7 having a full length amino acid sequence of SEQ ID NO: 8.

* * * * *

SEQUENCE LISTING

<160> NUMBER OF SEQ ID NOS: 10

<210> SEQ ID NO 1
<211> LENGTH: 1749
<212> TYPE: DNA
<213> ORGANISM: Aspergillus niger

<400> SEQUENCE: 1

```
tctaacggaa tcgaggcttc tttgttgaca gaccctaaag acgtttctgg aagaactgtc      60
gattacatca ttgccggtgg tggtttgacc ggattgacaa ctgccgctag attgaccgaa     120
aatccaaata tctctgtttt ggtcatcgag tctggatctt acgaatctga cagaggacca     180
attatcgagg atttgaacgc atacggtgac atcttcggtt cttctgttga tcatgcatac     240
gaaacagttg aattggctac taacaatcaa acagctttga ttagatctgg taacggattg     300
ggtggttcta cattggtcaa cggaggtact tggactagac cacataaggc ccaggtcgat     360
tcttgggaaa ctgtcttcgg aaacgaaggt tggaattggg ataatgttgc tgcatattct     420
ttgcaggcag aaagagctag agccccaaac gctaagcaaa ttgctgctgg tcattacttt     480
aatgcttctt gtcatggagt taacggtact gttcatgccg gaccaagaga tacaggtgac     540
gattactctc caattgttaa agccttgatg tctgctgttg aggatagagg tgtccctact     600
aagaaagact tggatgtggg tgacccacac ggtgtctcta tgttccctaa cacattgcat     660
gaggatcagg tcagatctga tgctgctaga gaatggttgt tgcctaatta ccaaagacca     720
aacttgcagg ttttgactgg tcagtatgtt ggaaaggtct tgttgtctca aaacggaact     780
accccaagag ccgttggagt cgaatttggt actcataagg gtaacactca caacgtttat     840
gctaaacatg aagttttgtt ggcagctggt tctgcagttt ctccaactat cttggaatac     900
tctggtattg gtatgaaatc tattttggag ccattgggta ttgatactgt cgttgatttg     960
ccagttggat tgaatttgca agaccagaca accgctacag ttagatctag aattacttct    1020
gccggagcag gacaaggaca ggctgcctgg ttcgctactt ttaacgagac ttttggtgac    1080
tattctgaga aggcacatga gttgttgaat actaagttgg aacagtgggc tgaagaggct    1140
gtcgcaagag gtggattcca caacactaca gcattgttga ttcaatatga gaactacaga    1200
gactggattg tcaaccataa cgttgcttac tctgaattgt ttttggatac agccggtgtt    1260
gcatctttcg acgtctggga tttgttgcca ttcacaagag gatacgttca catcttggat    1320
aaggatccat acttgcacca tttcgcctat gatccacaat acttcttgaa cgaattggac    1380
ttgttgggtc aagccgctgc aactcagttg gctagaaaca tttctaattc tggagctatg    1440
caaacttatt tcgcaggtga aactattcct ggtgacaatt tggcatatga cgcagatttg    1500
tctgcatgga ctgaatacat tccataccat tttagaccta actatcatgg tgtcggaact    1560
tgttctatga tgcctaagga aatgggtgga gttgtcgata acgccgccag agtctacggt    1620
gttcaaggtt tgagagttat tgatggatct attccaccaa cacaaatgtc ttctcatgtt    1680
atgacagtct tctacgctat ggcattgaaa atctctgacg caattttgga agattacgct    1740
tctatgcag                                                            1749
```

<210> SEQ ID NO 2
<211> LENGTH: 583
<212> TYPE: PRT
<213> ORGANISM: Aspergillus niger

<400> SEQUENCE: 2

Ser Asn Gly Ile Glu Ala Ser Leu Leu Thr Asp Pro Lys Asp Val Ser

-continued

```
1               5                   10                  15
Gly Arg Thr Val Asp Tyr Ile Ile Ala Gly Gly Leu Thr Gly Leu
                20                  25                  30
Thr Thr Ala Ala Arg Leu Thr Glu Asn Pro Asn Ile Ser Val Leu Val
                35                  40                  45
Ile Glu Ser Gly Ser Tyr Glu Ser Asp Arg Gly Pro Ile Ile Glu Asp
                50                  55                  60
Leu Asn Ala Tyr Gly Asp Ile Phe Gly Ser Ser Val Asp His Ala Tyr
65                  70                  75                  80
Glu Thr Val Glu Leu Ala Thr Asn Asn Gln Thr Ala Leu Ile Arg Ser
                85                  90                  95
Gly Asn Gly Leu Gly Gly Ser Thr Leu Val Asn Gly Gly Thr Trp Thr
                100                 105                 110
Arg Pro His Lys Ala Gln Val Asp Ser Trp Glu Thr Val Phe Gly Asn
                115                 120                 125
Glu Gly Trp Asn Trp Asp Asn Val Ala Ala Tyr Ser Leu Gln Ala Glu
                130                 135                 140
Arg Ala Arg Ala Pro Asn Ala Lys Gln Ile Ala Ala Gly His Tyr Phe
145                 150                 155                 160
Asn Ala Ser Cys His Gly Val Asn Gly Thr Val His Ala Gly Pro Arg
                165                 170                 175
Asp Thr Gly Asp Asp Tyr Ser Pro Ile Val Lys Ala Leu Met Ser Ala
                180                 185                 190
Val Glu Asp Arg Gly Val Pro Thr Lys Lys Asp Phe Gly Cys Gly Asp
                195                 200                 205
Pro His Gly Val Ser Met Phe Pro Asn Thr Leu His Glu Asp Gln Val
                210                 215                 220
Arg Ser Asp Ala Ala Arg Glu Trp Leu Leu Pro Asn Tyr Gln Arg Pro
225                 230                 235                 240
Asn Leu Gln Val Leu Thr Gly Gln Tyr Val Gly Lys Val Leu Leu Ser
                245                 250                 255
Gln Asn Gly Thr Thr Pro Arg Ala Val Gly Val Glu Phe Gly Thr His
                260                 265                 270
Lys Gly Asn Thr His Asn Val Tyr Ala Lys His Glu Val Leu Leu Ala
                275                 280                 285
Ala Gly Ser Ala Val Ser Pro Thr Ile Leu Glu Tyr Ser Gly Ile Gly
                290                 295                 300
Met Lys Ser Ile Leu Glu Pro Leu Gly Ile Asp Thr Val Val Asp Leu
305                 310                 315                 320
Pro Val Gly Leu Asn Leu Gln Asp Gln Thr Thr Ala Thr Val Arg Ser
                325                 330                 335
Arg Ile Thr Ser Ala Gly Ala Gly Gln Gly Gln Ala Ala Trp Phe Ala
                340                 345                 350
Thr Phe Asn Glu Thr Phe Gly Asp Tyr Ser Glu Lys Ala His Glu Leu
                355                 360                 365
Leu Asn Thr Lys Leu Glu Gln Trp Ala Glu Glu Ala Val Ala Arg Gly
                370                 375                 380
Gly Phe His Asn Thr Thr Ala Leu Leu Ile Gln Tyr Glu Asn Tyr Arg
385                 390                 395                 400
Asp Trp Ile Val Asn His Asn Val Ala Tyr Ser Glu Leu Phe Leu Asp
                405                 410                 415
Thr Ala Gly Val Ala Ser Phe Asp Val Trp Asp Leu Leu Pro Phe Thr
                420                 425                 430
```

-continued

```
Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580
```

```
<210> SEQ ID NO 3
<211> LENGTH: 45
<212> TYPE: DNA
<213> ORGANISM: Artificial Sequence
<220> FEATURE:
<223> OTHER INFORMATION: Synthetically generated primer

<400> SEQUENCE: 3
gggaaactgt cttcggaaac ccaggttgga attgggataa tgttg              45

<210> SEQ ID NO 4
<211> LENGTH: 45
<212> TYPE: DNA
<213> ORGANISM: Artificial Sequence
<220> FEATURE:
<223> OTHER INFORMATION: Synthetically generated primer

<400> SEQUENCE: 4
ctaattacca aagaccaaac ttggttgttt tgactggtca gtatg              45

<210> SEQ ID NO 5
<211> LENGTH: 1749
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 5
tctaacggaa tcgaggcttc tttgttgaca gaccctaaag acgtttctgg aagaactgtc      60
gattacatca ttgccggtgg tggtttgacc ggattgacaa ctgccgctag attgaccgaa     120
aatccaaata tctctgtttt ggtcatcgag tctggatctt acgaatctga cagaggacca     180
attatcgagg atttgaacgc atacggtgac atcttcggtt cttctgttga tcatgcatac     240
gaaacagttg aattggctac taacaatcaa acagctttga ttagatctgg taacggattg     300
ggtggttcta cattggtcaa cggaggtact tggactagac cacataaggc ccaggtcgat     360
tcttgggaaa ctgtcttcgg aaacccaggt tggaattggg ataatgttgc tgcatattct     420
```

```
ttgcaggcag aaagagctag agccccaaac gctaagcaaa ttgctgctgg tcattacttt    480
aatgcttctt gtcatggagt taacggtact gttcatgccg gaccaagaga tacaggtgac    540
gattactctc caattgttaa agccttgatg tctgctgttg aggatagagg tgtccctact    600
aagaaagact ttggatgtgg tgacccacac ggtgtctcta tgttccctaa cacattgcat    660
gaggatcagg tcagatctga tgctgctaga gaatggttgt tgcctaatta ccaaagacca    720
aacttgcagg ttttgactgg tcagtatgtt ggaaaggtct tgttgtctca aaacggaact    780
accccaagag ccgttggagt cgaatttggt actcataagg gtaacactca aacgtttat    840
gctaaacatg aagttttgtt ggcagctggt tctgcagttt ctccaactat cttggaatac    900
tctggtattg gtatgaaatc tattttggag ccattgggta ttgatactgt cgttgatttg    960
ccagttggat tgaatttgca agaccagaca accgctacag ttagatctag aattacttct   1020
gccggagcag acaaggaca ggctgcctgg ttcgctactt taacgagac ttttggtgac   1080
tattctgaga aggcacatga gttgttgaat actaagttgg aacagtgggc tgaagaggct   1140
gtcgcaagag gtggattcca caacactaca gcattgttga ttcaatatga gaactacaga   1200
gactggattg tcaaccataa cgttgcttac tctgaattgt ttttggatac agccggtgtt   1260
gcatctttcg acgtctggga tttgttgcca ttcacaagag gatacgttca catcttggat   1320
aaggatccat acttgcacca tttcgcctat gatccacaat acttcttgaa cgaattggac   1380
ttgttgggtc aagccgctgc aactcagttg gctagaaaca tttctaattc tggagctatg   1440
caaacttatt tcgcaggtga actattcct ggtgacaatt tggcatatga cgcagatttg   1500
tctgcatgga ctgaatacat tccataccat tttagaccta actatcatgg tgtcggaact   1560
tgttctatga tgcctaagga aatgggtgga gttgtcgata acgccgccag agtctacggt   1620
gttcaaggtt tgagagttat tgatggatct attccaccaa cacaaatgtc ttctcatgtt   1680
atgacagtct tctacgctat ggcattgaaa atctctgacg caattttgga agattacgct   1740
tctatgcag                                                           1749
```

<210> SEQ ID NO 6
<211> LENGTH: 583
<212> TYPE: PRT
<213> ORGANISM: Artificial Sequence
<220> FEATURE:
<223> OTHER INFORMATION: Sequence synthetically translated from SEQ ID NO: 5

<400> SEQUENCE: 6

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Thr Gly Leu
                20                  25                  30

Thr Thr Ala Ala Arg Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
            115                 120                 125

Pro Gly Trp Asn Trp Asp Asn Val Ala Ala Tyr Ser Leu Gln Ala Glu
130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
            165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
            195                 200                 205

Pro His Gly Val Ser Met Phe Pro Asn Thr Leu His Glu Asp Gln Val
            210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
            245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
            275                 280                 285

Ala Gly Ser Ala Val Ser Pro Thr Ile Leu Glu Tyr Ser Gly Ile Gly
            290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
            325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
            355                 360                 365

Leu Asn Thr Lys Leu Glu Gln Trp Ala Glu Glu Ala Val Ala Arg Gly
            370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
            405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
            435                 440                 445

Ala Tyr Asp Pro Gln Tyr Phe Leu Asn Glu Leu Asp Leu Leu Gly Gln
            450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
            485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
            515                 520                 525

Gly Gly Val Val Asp Asn Ala Ala Arg Val Tyr Gly Val Gln Gly Leu

```
                530                 535                 540
Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
                580

<210> SEQ ID NO 7
<211> LENGTH: 1749
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 7
tctaacggaa tcgaggcttc tttgttgaca gaccctaaag acgtttctgg aagaactgtc      60
gattacatca ttgccggtgg tggtttgacc ggattgacaa ctgccgctag attgaccgaa     120
aatccaaata tctctgtttt ggtcatcgag tctggatctt acgaatctga cagaggacca     180
attatcgagg atttgaacgc atacggtgac atcttcggtt cttctgttga tcatgcatac     240
gaaacagttg aattggctac taacaatcaa acagctttga ttagatctgg taacggattg     300
ggtggttcta cattggtcaa cggaggtact tggactagac acataaggc ccaggtcgat      360 tcttgggaaa ctgtcttcgg aaacgaaggt tggaattggg ataatgttgc tgcatattct     420
ttgcaggcag aaagagctag agccccaaac gctaagcaaa ttgctgctgg tcattacttt     480
aatgcttctt gtcatggagt taacggtact gttcatgccg gaccaagaga tacaggtgac     540
gattactctc caattgttaa agccttgatg tctgctgttg aggatagagg tgtccctact     600
aagaaagact ttggatgtgg tgacccacac ggtgtctcta tgttccctaa cacattgcat     660
gaggatcagg tcagatctga tgctgctaga gaatggttgt tgcctaatta ccaaagacca     720
aacttggttg ttttgactgg tcagtatgtt ggaaaggtct tgttgtctca aaacggaact     780
accccaagag ccgttggagt cgaatttggt actcataagg gtaacactca aacgttttat     840
gctaaacatg aagttttgtt ggcagctggt tctgcagttt ctccaactat cttggaatac     900
tctggtattg gtatgaaatc tattttggag ccattgggta ttgatactgt cgttgatttg     960
ccagttggat tgaatttgca agaccagaca accgctacag ttagatctag aattacttct    1020
gccggagcag gacaaggaca ggctgcctgg ttcgctactt ttaacgagac ttttggtgac    1080
tattctgaga aggcacatga gttgttgaat actaagttgg aacagtgggc tgaagaggct    1140
gtcgcaagag gtggattcca aacactaca gcattgttga ttcaatatga gaactacaga     1200
gactggattg tcaaccataa cgttgcttac tctgaattgt ttttggatac agccggtgtt    1260
gcatctttcg acgtctggga tttgttgcca ttcacaagag gatacgttca catcttggat    1320
aaggatccat acttgcacca tttcgcctat gatccacaat acttcttgaa cgaattggac    1380
ttgttgggtc aagccgctgc aactcagttg gctagaaaca tttctaattc tggagctatg    1440
caaacttatt tcgcaggtga actattcct ggtgacaatt ggcatatga cgcagatttg      1500 tctgcatgga ctgaatacat tccataccat tttagaccta actatcatgg tgtcggaact    1560
tgttctatga tgcctaagga aatgggtgga gttgtcgata acgccgccag agtctacggt    1620
gttcaaggtt tgagagttat tgatggatct attccaccaa cacaaatgtc ttctcatgtt    1680
atgacagtct tctacgctat ggcattgaaa atctctgacg caatttggga agattacgct    1740
```

```
tctatgcag                                                         1749
```

<210> SEQ ID NO 8
<211> LENGTH: 583
<212> TYPE: PRT
<213> ORGANISM: Artificial Sequence
<220> FEATURE:
<223> OTHER INFORMATION: Sequence synthetically translated from SEQ ID
      NO: 7

<400> SEQUENCE: 8

```
Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Thr Gly Leu
            20                  25                  30

Thr Thr Ala Ala Arg Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Leu Val Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350
```

```
Thr Phe Asn Glu Thr Phe Gly Asp Tyr Ser Glu Lys Ala His Glu Leu
            355                 360                 365
Leu Asn Thr Lys Leu Glu Gln Trp Ala Glu Glu Ala Val Ala Arg Gly
        370                 375                 380
Gly Phe His Asn Thr Thr Ala Leu Leu Ile Gln Tyr Glu Asn Tyr Arg
385                 390                 395                 400
Asp Trp Ile Val Asn His Asn Val Ala Tyr Ser Glu Leu Phe Leu Asp
                405                 410                 415
Thr Ala Gly Val Ala Ser Phe Asp Val Trp Asp Leu Leu Pro Phe Thr
            420                 425                 430
Arg Gly Tyr Val His Ile Leu Asp Lys Asp Pro Tyr Leu His His Phe
        435                 440                 445
Ala Tyr Asp Pro Gln Tyr Phe Leu Asn Glu Leu Asp Leu Leu Gly Gln
    450                 455                 460
Ala Ala Ala Thr Gln Leu Ala Arg Asn Ile Ser Asn Ser Gly Ala Met
465                 470                 475                 480
Gln Thr Tyr Phe Ala Gly Glu Thr Ile Pro Gly Asp Asn Leu Ala Tyr
                485                 490                 495
Asp Ala Asp Leu Ser Ala Trp Thr Glu Tyr Ile Pro Tyr His Phe Arg
            500                 505                 510
Pro Asn Tyr His Gly Val Gly Thr Cys Ser Met Met Pro Lys Glu Met
        515                 520                 525
Gly Gly Val Val Asp Asn Ala Ala Arg Val Tyr Gly Val Gln Gly Leu
    530                 535                 540
Arg Val Ile Asp Gly Ser Ile Pro Pro Thr Gln Met Ser Ser His Val
545                 550                 555                 560
Met Thr Val Phe Tyr Ala Met Ala Leu Lys Ile Ser Asp Ala Ile Leu
                565                 570                 575
Glu Asp Tyr Ala Ser Met Gln
            580
```

<210> SEQ ID NO 9
<211> LENGTH: 1749
<212> TYPE: DNA
<213> ORGANISM: Artificial Sequence
<220> FEATURE:
<223> OTHER INFORMATION: Synthetically generated DNA encoding a modified enzyme

<400> SEQUENCE: 9

```
tctaacggaa tcgaggcttc tttgttgaca gaccctaaag acgtttctgg aagaactgtc      60
gattacatca ttgccggtgg tggtttgacc ggattgacaa ctgccgctag attgaccgaa     120
aatccaaata tctctgtttt ggtcatcgag tctggatctt acgaatctga cagaggacca     180
attatcgagg atttgaacgc atacggtgac atcttcggtt cttctgttga tcatgcatac     240
gaaacagttg aattggctac taacaatcaa acagctttga ttagatctgg taacggattg     300
ggtggttcta cattggtcaa cggaggtact tggactagac cacataaggc ccaggtcgat     360
tcttgggaaa ctgtcttcgg aaacccaggt tggaattggg ataatgttgc tgcatattct     420
tgcaggcag aaagagctag agccccaaac gctaagcaaa ttgctgctgg tcattacttt     480
aatgcttctt gtcatggagt taacggtact gttcatgccg gaccaagaga tacaggtgac     540
gattactctc caattgttaa agccttgatg tctgctgttg aggatagagg tgtccctact     600
aagaaagact ttggatgtgg tgacccacac ggtgtctcta tgttccctaa cacattgcat     660
```

```
gaggatcagg tcagatctga tgctgctaga gaatggttgt tgcctaatta ccaaagacca    720
aacttggttg ttttgactgg tcagtatgtt ggaaaggtct tgttgtctca aaacggaact    780
accccaagag ccgttggagt cgaatttggt actcataagg gtaacactca caacgtttat    840
gctaaacatg aagttttgtt ggcagctggt tctgcagttt ctccaactat cttggaatac    900
tctggtattg gtatgaaatc tattttggag ccattgggta ttgatactgt cgttgatttg    960
ccagttggat tgaatttgca agaccagaca accgctacag ttagatctag aattacttct   1020
gccggagcag gacaaggaca ggctgcctgg ttcgctactt taacgagac ttttggtgac   1080 tattctgaga aggcacatga gttgttgaat actaagttgg aacagtgggc tgaagaggct   1140
gtcgcaagag gtggattcca caacactaca gcattgttga ttcaatatga aactacaga   1200 gactggattg tcaaccataa cgttgcttac tctgaattgt ttttggatac agccggtgtt   1260
gcatctttcg acgtctggga tttgttgcca ttcacaagag gatacgttca catcttggat   1320
aaggatccat acttgcacca tttcgcctat gatccacaat acttcttgaa cgaattggac   1380
ttgttgggtc aagccgctgc aactcagttg gctagaaaca tttctaattc tggagctatg   1440
caaacttatt tcgcaggtga aactattcct ggtgacaatt tggcatatga cgcagatttg   1500
tctgcatgga ctgaatacat tccataccat tttagaccta actatcatgg tgtcggaact   1560
tgttctatga tgcctaagga aatgggtgga gttgtcgata acgccgccag agtctacggt   1620
gttcaaggtt tgagagttat tgatggatct attccaccaa cacaaatgtc ttctcatgtt   1680
atgacagtct tctacgctat ggcattgaaa atctctgacg caattttgga agattacgct   1740
tctatgcag                                                           1749
```

<210> SEQ ID NO 10
<211> LENGTH: 583
<212> TYPE: PRT
<213> ORGANISM: Artificial Sequence
<220> FEATURE:
<223> OTHER INFORMATION: Sequence synthetically translated from SEQ ID
      NO: 9

<400> SEQUENCE: 10

```
Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Thr Gly Leu
                20                  25                  30

Thr Thr Ala Ala Arg Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Pro Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160
```

-continued

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Val Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
    290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Ala Ala Trp Phe Ala
            340                 345                 350

Thr Phe Asn Glu Thr Phe Gly Asp Tyr Ser Glu Lys Ala His Glu Leu
        355                 360                 365

Leu Asn Thr Lys Leu Glu Gln Trp Ala Glu Glu Ala Val Ala Arg Gly
    370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

```
Glu Asp Tyr Ala Ser Met Gln
            580
```